United States Patent [19]
Majoros et al.

[11] Patent Number: 5,840,814
[45] Date of Patent: Nov. 24, 1998

[54] MULTI-ARM STAR POLYMERS HAVING A WELL-DEFINED CORE AND METHODS FOR THE SYNTHESIS THEREOF

[75] Inventors: Istvan J. Majoros; Timea M. Marsalko, both of Stow; Joseph P. Kennedy, Akron, all of Ohio

[73] Assignee: The University of Akron, Akron, Ohio

[21] Appl. No.: 693,418

[22] Filed: Aug. 7, 1996

[51] Int. Cl.$^6$ ............... C08G 85/00; C08G 77/38
[52] U.S. Cl. ............ 525/502; 525/101; 525/106; 525/138; 525/145
[58] Field of Search .................. 525/502, 480, 525/101, 106, 138, 145

[56] References Cited

U.S. PATENT DOCUMENTS

| | | | |
|---|---|---|---|
| 4,636,539 | 1/1987 | Harris et al. | 523/214 |
| 4,957,960 | 9/1990 | Harris et al. | 524/243 |
| 5,003,004 | 3/1991 | Simms | 525/68 |
| 5,057,576 | 10/1991 | Spinelli | 525/267 |
| 5,143,784 | 9/1992 | Mita | 428/336 |
| 5,247,026 | 9/1993 | Erickson et al. | 525/331.9 |
| 5,274,065 | 12/1993 | Veith | 528/26 |
| 5,276,095 | 1/1994 | Hoxmeier | 525/105 |
| 5,310,490 | 5/1994 | Struglinski et al. | 252/43 |
| 5,310,814 | 5/1994 | Struglinski et al. | 525/314 |
| 5,314,960 | 5/1994 | Spinelli et al. | 525/280 |
| 5,314,961 | 5/1994 | Anton et al. | 525/280 |
| 5,371,147 | 12/1994 | Spinelli et al. | 525/288 |
| 5,382,604 | 1/1995 | Erickson | 522/158 |
| 5,395,885 | 3/1995 | Kennedy et al. | 525/98 |
| 5,428,114 | 6/1995 | Erickson et al. | 525/331.9 |
| 5,458,796 | 10/1995 | Storey et al. | 252/58 |

OTHER PUBLICATIONS

"Calixarenes. 4. The Synthesis, Characterization, and Properties of the Calixarenes from p–tert–Buthylphenol" by Gutsche et al., *J. A. Chem. Soc.*, 103, pp. 3782–3792 (1981).

"Calixarenes 12 The Synthesis of Functionalized Calixarenes" by Gutsche et al., *Tetahedron*, vol. 42, No. 6, pp. 1633–1640 (1986).

"Calixarenes, 19 Studies of the formation of calixarenes via condensation of p–alkylphenols and formaldehyde" by Dhawan et al., *Makromol. Chem*, 188, pp. 921–950 (1987).

"Ferrocenyl Substituted Ocatakis(dimethylsiloxy)octasilsesquioxanes: A New Class of Supramolecular Organometallic Compounds. Synthesis, Characterization, and Electrochemistry" by Moran et al. *Organometallics*, vol. 12, No. 11, pp. 4327–4333 (1993).

"Synthesis and characterization of monofunctional polydimethylsiloxanes with a narrow molecular weight distribution" by Hammouch et al., *Polymer*, vol. 36, No. 2, pp. 421–426 (1995).

*Primary Examiner*—Ralph H. Dean
*Attorney, Agent, or Firm*—Renner, Kenner, Greive, Bobak Taylor & Weber

[57] ABSTRACT

The synthesis of star polymers having well-defined arms emanating from well-defined and readily controllable calix [n]arene (n=4 to 16) cores are described. The synthesis is particularly suitable for polyisobutylene and/or polysiloxane star polymers. The synthesis has been achieved using carbocationic and/or anionic ring-opening polymerization techniques to form polymer arms of desired molecular weights, then separately preparing the calixarene derivative core, and finally, linking the arms to the core by transesterification or hydrosilation.

27 Claims, 5 Drawing Sheets

MULTI-ARM STAR POLYMERS HAVING A WELL-DEFINED CORE AND METHODS FOR THE SYNTHESIS THEREOF

The research disclosed in this application was at least partially supported by the National Science Foundation under Grant 94-23202.

TECHNICAL FIELD

This invention relates generally to star polymers and, more particularly, to the synthesis of star polymers having multiple, well-defined arms emanating from well-defined cores. Specifically, this invention relates to the synthesis of well-defined star polymers having multiple, well-defined arms of polyisobutylene, polysiloxane and the like emanating from a calixarene core. The synthesis is accomplished by separately preparing (1) appropriately terminated polyisobutylenes and/or polysiloxanes and (2) a compatible calixarene derivative suitable for linking with the appropriately terminated polyisobutylene and/or polysiloxane, and then linking a plurality of polyisobutylene and/or polysiloxane arms to the calixarene core. The resultant star polymers have a well-defined core as well as well-defined arms and are seen as being highly desirable as viscosity modifiers and oil additives since they are less sensitive to oxidative reactions and may be more shear stable than prior art star polymers.

BACKGROUND OF THE INVENTION

The synthesis of various multi-arm radial or star polymers have become of growing practical and theoretical interest to a variety of industries. Such star polymers may be useful as, inter alia, surfactants, lubricants, rheology modifiers, and viscosity modifiers. In fact, star polymers are now considered by many to be state-of-the-art viscosity modifiers and oil additives, although the potential of some of these star polymers for such applications is still being evaluated and tested.

One well-known representative of this class of materials, currently being used as an oil additive, is commercially available from the Shell Oil Co. (Houston, Tex.) under the tradename Shelvis. This oil additive is a multi-arm star molecule consisting of many hydrogenated polyisoprene arms emanating from a core of crosslinked polydivinylbenzene (PDVB).

Although generally believed to be an excellent oil additive, Shelvis, nevertheless, has some undesirable characteristics due principally to the use of an ill-defined core, namely PDVB. By the term "ill-defined" it is meant that the core, e.g., PDVB, is an uncontrolled, crosslinked, gel-like structure having unsaturation sites in the core. That is, there are double bonds in the PDVB which prevent the core structure from being readily characterized or the resultant star polymer from being controlled. Furthermore, the structure of PDVB makes the core insoluble in most solvents and, therefore, gel-like until it is linked to the polyisoprene arms which permit the entire polymer to solubilize. In comparison, "well-defined" cores are built of readily characterizable, controlled, saturated, soluble molecules which are precursors to the core. As a result, the structure of the well-defined core as well as the structure of the resultant star polymers can be controlled.

Still further, the arms of Shelvis are made by hydrogenation of polyisoprene, an expensive and hazardous process. Furthermore, this process is never complete since about 4 percent of the double bonds in polyisoprene remain unhydrogenated, and the surviving unsaturations, in both the arms and the core, may impart oxidative and thermal vulnerability to the product. That is, the presence of unsaturation sites in the arms and/or the core provides for the possibility that the resultant star polymers will be more sensitive to oxidative reactions than star polymers having well-defined arms emanating from well-defined cores. Thus, in engine oil, where sensitivity to oxidation may be of critical importance, the possibility exists that during use, the ill-defined arms and/or cores will undergo oxidative degradation. Furthermore, where the arms of the polymer remain unsaturated, the possibility exists that during high temperature and heavy shear in the engine, the arms may even decompose.

To date, considerable efforts have been made to prepare star-like structures having arms made of various materials and ranging in number from about 2 to at least as many as 250 or more. In doing so, three major techniques or processes have evolved for the synthesis of these star polymers. These three techniques are typically distinguished from each other by (1) the sequential copolymerization/linking with a divinyl monomer, known as the "arm-first" method, (2) the use of multifunctional initiators, known as the "core-first" method, and (3) the use of multifunctional linking agents and/or reactions, known as the "arm and core first" method.

Linking living polymer chains with divinyl monomer(s) is well known. For example, Kennedy et al. U.S. Pat. No. 5,395,885 used this technique to first synthesize star polymers consisting of polyisobutylene arms emanating from PDVB cores. The synthesis of the arms was carried out using cationic polymerization techniques. Various other studies have also used this "arm-first" technique for the synthesis of multi-arm stars by anionic and group transfer polymerization techniques as well.

The use of multifunctional initiators for the synthesis of multi-arm stars is also well known, although their use has been somewhat limited due to solubility problems, especially in anionic polymerizations. However, these solubility problems appear to be less severe with cationic polymerizations, and di-, tri-, and tetra-functional initiators have been used to prepare well-defined two-, three-, and four-arm star polymers under certain conditions and with certain initiators.

With respect to the use of multifunctional linking agents, such agents have proven useful, in conjunction with anionic polymerization techniques, in preparing homo-, block- and hetero-arm star polymers with various numbers of arms. However, only a few multifunctional linking agents have been used in conjunction with carbocationic polymerization techniques. In either case (using anionic or carbocationic polymerization techniques) well-defined cores might be obtained, but there was little significant improvement in the oxidative or thermal stability of the resultant star polymer.

For example, carbocationic polymerizations have been carried out in conjunction with this "arm and core-first" method to prepare well-defined tetra-arm poly(isobutyl vinyl ether) stars, multi-arm polyisobutylene stars with siloxane cores, and polysiloxane stars with siloxane cores. In the case of the polyisobutylene and polysiloxane stars, the stars were prepared by hydrosilation of allyl-terminated polyisobutylenes or polysiloxanes with siloxane cores.

Thus, because of the potential limitations of siloxane cores, methods for the synthesis of multi-arm star polymers having well-defined cores suitable for use with various polymer systems, including polyisobutylenes and polysiloxanes, is still highly desired. In the present invention, calixarenes are seen as a potential solution to the existing problems of ill-defined cores and to the limitations of other well-defined cores. Calixarenes are cyclic condensation products of p-substituted phenol and formaldehyde. Various procedures have been developed by Gutsche et al. for the selective synthesis of various calixarenes and calixarene derivatives. Detailed descriptions of these procedures are set forth in various publications by Gutsche et al., including Gutsche, C. D., *Calixarenes,* The Royal Society of Chemistry, Thomas Graham House, Cambridge, (1989); Gutsche, C. D. et al. "Calixarenes. 4. The Synthesis, Characterization, and Properties of the Calixarenes for p-tert-Butylphenol", *J. Am. Chem. Soc.* 103, 3782 (1981); and Gutsche, C. D. and L. G. Lin, "Calixarenes. 12. The Synthesis of Functionalized Calixarenes" *Tetrahedron* 42(6), 1633 (1986), the disclosures of each of which are incorporated herein by reference. To date, it is known that Gutsche and others have produced calix[n]arenes, where n=4 to 16. Calixarenes are known to be more oxidative and thermally stable than siloxanes, and they have the possibility of bonding with second materials, such as metals or dyes, to enhance their potential use in various applications, such as paints, oils and the like.

It will be appreciated that, while polyisobutylenes, polysiloxanes, and calixarenes are well-known in the art, these moieties have not, heretofore, ever been combined into multi-arm stars. That is, the art has not heretofore provided a means for the synthesis of any star polymers, including polyisobutylene or polysiloxane stars, having well-defined calixarene cores. Thus, the need exists for a method of synthesizing star polymers having well-defined polymer arms emanating from well-defined calixarene cores.

SUMMARY OF INVENTION

It is therefore, an object of the present invention to provide a star polymer having a plurality of well-defined arms emanating from a well-defined calixarene core.

It is another object of the present invention to provide a star polymer, as above, having a plurality of polyisobutylene and/or polysiloxane arms emanating from a calix[n]arene (n=4 to 16) core.

It is yet another object of the present invention to provide a star polymer, as above, wherein the core is more resistant to oxidative and/or thermal degradation and is capable of bonding to a second material.

It is still another object of the present invention to provide a star polymer, as above, which is generally more resistant to oxidative degradation and may be more shear stable than other star polymers having ill-defined cores or partially unsaturated arms.

It is a further object of the present invention to provide a method for the synthesis of star polymers comprising a calixarene derivative core.

It is still a further object of the present invention to provide a method for the synthesis of star polymers, as above, which uses a less expensive and less hazardous process than hydrogenation.

It is yet a further object of the present invention to provide a method for the synthesis of star polymers, as above, using carbocationic polymerization techniques in conjunction with the "arm and core-first" method.

It is still a further object of the present invention to provide a method for the synthesis of star polymers having well-defined polyisobutylene and/or polysiloxane arms emanating from well-defined calixarene cores.

At least one or more of the foregoing objects, together with the advantages thereof over the known art relating to multi-arm star polymers and the synthesis thereof, which shall become apparent from the specification which follows, are accomplished by the invention as hereinafter described and claimed.

In general the present invention provides a star polymer comprising a well-defined core component selected from the group consisting of calix[n]arenes where n=4 to 16 and derivatives thereof; and a plurality of polymer arms connected to the core component. Preferably, at least one of the polymer arms is selected from the group consisting of polyisobutylene and polysiloxane.

Other objects and aspects of the invention which will become apparent herein are attained by a method for the synthesis of polyisobutylene star polymers comprising linking a plurality of hydroxyl-terminated polyisobutylene arms to a core component selected from the group consisting of calixarenes and derivatives thereof, wherein the core component has from about 4 to 16 member units and includes at least one functional ester group extending from each member unit, each polyisobutylene arm being linked to one of the ester groups of the core component by transesterification in the presence of a catalyst.

Still other objects and aspects of the invention which will become apparent herein are attained by a method for the synthesis of polysiloxane star polymers comprising linking a plurality of SiH-terminated polysiloxane arms to a core component selected from the group consisting of calixarenes and derivatives thereof, wherein the core component has from about 4 to 16 member units and includes at least one functional allyl group extending from each member unit, each polysiloxane arm being linked to one of the allyl groups of the core component by hydrosilation in the presence of a catalyst.

The present invention further includes a method for the synthesis of star polymers containing polyisobutylene and polysiloxane arms emanating from a core, comprising linking a plurality of hydroxyl-terminated polyisobutylene arms and a plurality of SiH-terminated polysiloxane arms to a core component selected from the group consisting of calixarenes and derivatives thereof, wherein the core component has from about 4 to 16 member units and includes at least one functional ester group extending from each member unit and at least one functional allyl group extending from each member unit, each polyisobutylene arm being linked to one of the ester groups of the core component by transesterification in the presence of a first catalyst, and each polysiloxane arm being linked to one of the allyl groups of the core component by hydrosilation in the presence of a second catalyst.

PREFERRED EMBODIMENT FOR CARRYING OUT THE INVENTION

Broadly, the present invention is directed toward the production or synthesis of multi-arm star polymers, each having a structure comprising a ring-shaped or cyclic first component, referred to hereinafter as a "core", selected from the group consisting of calix[n]arenes, where n=4 to 16, and derivatives thereof, connected to a plurality of second components, referred to hereinafter as the "arms". The arms extend outwardly or radially from the core so as to form a star-like structure. Hence, the term "star polymer" is used to describe these multi-arm types of compositions.

In the preferred embodiments, the arms are selected from the group consisting of polyisobutylene, polysiloxane or both, which arms emanate from well-defined cores of calixarene derivatives. By the term "well-defined", it is meant that the core of the star polymer has a chemical structure wherein all of the reactive sites for the core are known and can be controlled. That is, unlike polydivinylbenzene (PDVB) cores which are complex networks whose detailed structural characterization is nearly impossible, there are no unreacted double bonds in the calixarene derivative core to impart oxidative or thermal vulnerability to the resultant product, meaning the resultant product is not sensitive to oxidation. In fact, the calixarene cores of the present invention have been found to be even more resistant to oxidation and thermal degradation than certain other well-defined cores such as siloxanes. These cores are seen as being further beneficial to the extent that they are capable of bonding with other materials such as metals or the like, which may enhance their potential for use in applications beyond viscosity modifiers.

The synthesis of these new star polymers has been accomplished by the "arm and core first" method disclosed hereinabove. That is, the multi-arm star polymers are prepared in essentially three separate steps—(1) preparation of the appropriately terminated polyisobutylene or polysiloxane arms, (2) preparation of the appropriate calixarene derivative core suitable for use with the particular arms desired, and (3) linking the arms to the core. Each of these steps are more particularly discussed hereinbelow with respect to the preferred embodiment for carrying out the invention.

(I) PREPARATION OF ARMS

A. Polyisobutylene Arms

Polyisobutylene (PIB) arms suitable for linking to calixarene cores according to the concepts of the present invention may be any hydroxyl-terminated polyisobutylene of any desired molecular weight. More preferably, arms, or "pre-arms" since they are not yet connected to the core, selected from the group consisting of monohydroxyl-terminated polyisobutylenes are used.

Hydroxyl-terminated polyisobutylenes, and particularly monohydroxyl-terminated polyisobutylenes (PIB-OH), are well known in the art and may be prepared for the present invention by any manner known in the art. However, it has been found that "living" carbocationic polymerization of isobutylene is particularly suitable since the "prearm" can be prepared under certain conditions to practically any length desired (and, therefore, to practically any molecular weight desired) when followed by quantitative end-functionalization to the —OH terminus. A detailed description of the well-known carbocationic polymerization process is more specifically set forth in, inter alia, Kennedy, J. P. and B. Ivan, *Designed Polymers by Carbocationic Macromolecular Engineering, Theory and Practice,* Hanser Publishers, Munich, Germany (1992); Ivan, B., J. P. Kennedy and V. S. C. Chang, "New Telechelic Polymers and Sequential Copolymer by Polyfunctional Initiator-Transfer Agents (Inifers) VII. Synthesis and Characterization of α,ω-(Dihydroxyl)polyisobutylene," *J. Polymer Sci. Polym. Chem. Ed.,* 18, 3177–3193 (1980); Ivan, B. and J. P. Kennedy, "Living Carbocationic Polymerization. XX. Synthesis of Allyl-Telechelic Polyisobutylenes by One-Pot Polymerization-Functionalization," *Polym. Mat. Sci. Eng.,* 58, 869–872 (1988); and Majoros, I. et al., "Conventional and Living Carbocationic Polymerization United. I. A Comprehensive Model and New Diagnostic Method to Probe the Mechanism of Homopolymerizations," *Adv. Polym. Sci.,* 112, 1–114 (1994), the disclosures of which are incorporated herein by reference.

In the preferred embodiment, monohydroxyl-terminated polyisobutylenes having the basic structures:

wherein R is essentially any carbocationic polymerization initiator which will not sterically hinder the resultant polymer or polymer star are preferred. More preferably, R may be selected from the group consisting of tert-butyl, cumyl, p-methyl cumyl, p-methoxy cumyl, and p-(β-bromo-ethyl) cumyl, all well-known polymerization initiators.

As noted hereinabove, the resultant hydroxyl-terminated polyisobutylenes may be of any desired molecular weight, but preferably, will have a number average molecular weight of from about 500 to about 2,000,000 g/mol, although larger or smaller units may be employed depending upon the circumstances involved.

B. Polysiloxane Arms

Polysiloxane arms or "prearms" suitable for linking to calixarene cores are preferably selected from the group consisting of SiH-terminated polysiloxanes of any desired molecular weight, and more preferably, are selected from the group consisting of SiH-terminated polydimethylsiloxanes (PDMS-SiH). Polysiloxanes, and particularly PDMS, are well-known in the art and may be prepared for the present invention by any manner known in the art. However, as with PIB-OH, it has been found that anionic ring-opening polymerization of siloxane is particularly suitable since the "prearm" can be prepared under certain conditions to practically any length or molecular weight desired when followed by quantitative end-functionalization to the —SiH terminus. A detailed description of a preferred route for the anionic ring-opening synthesis of polydimethylsiloxane is more specifically set forth in Hammouch, S. O., et al., "Synthesis and Characterization of Monofunctional Polydimethylsiloxanes with a Narrow Molecular Weight Distribution," *Polymer*, 32(2), 421–426 (1995), the disclosure of which is incorporated herein by reference. Additional synthetic routes for other polysiloxanes are set forth in Bazant, V. et al., *Organosilicon Compounds* Academic Press, New York, N.Y. (1965); Fordham, S., *Silicones*, William Clowes and Sons, London, England (1960); and *Silicon Compounds Register and Review*, Petrarch Systems, Inc, Bristol, Conn. (?) (1982), the disclosures of which are also incorporated herein by reference.

Preferably, any SiH-terminated polysiloxane arms having the basic structure:

where sec-butyl is essentially the anionic polymerization initiator, and where $R_2$ and $R_3$ may be the same or different aryl or alkyl groups having from 1 to about 6 carbon atoms, can be used. In the preferred embodiment, PDMS-SiH having the structure is used. The synthesis of this structure using anionic polymerization techniques is also well known in the art and may even be commercially available in some areas.

Like the polyisobutylenes above, the molecular weights of these arms can be readily controlled by the noted anionic polymerization techniques. Thus, while the resultant SiH-terminated polysiloxanes may be of any desired molecular weight, and preferably, will have a number average molecular weight of from about 500 to about 2,000,000 g/mol, larger or smaller units may be employed depending upon the circumstances involved.

(II) PREPARATION OF CORES

Generally, the use of calixarenes and derivatives thereof as well-defined cores in the production of new star polymers is believed unique to the present invention. Accordingly, it will be appreciated that the present invention is not necessarily limited to those star polymers having polyisobutylene or polysiloxane arms, but rather, may be inclusive of other appropriately terminated homo-, hetero-, co-, random- or block-polymer suitable for use in connection with the calixarenes or derivatives thereof.

Calixarenes and derivatives thereof which are suitable for use in the present invention are dependent upon the type or types of arms to be used in the production of the star polymer as well as the number of arms desired. That is, the selection of which calixarene derivative should be used in the production of the star polymer is based upon the type(s) of polymer arms desired, while the number of polymer arms, N, will depend upon (1) the number of cyclic member units, n, in the calixarene product since each member unit will have at least one, and possibly, two or more reactive sites, and (2) the number of appropriate functional groups attached to each member unit.

It is conventional in the art to refer to the number of member units found in the cyclic calixarene by denoting the product as calix[n]arene where n equals the number of cyclic member units. In the present invention, calix[n]arenes, where n equals from about 4 to about 16, are preferred. More preferably, however, are calix[n]arenes having about 6 to about 16 member units, i.e., n=6 to 16. Particularly preferred are those calix[n]arenes where n=4, 6, or 8.

It will be appreciated that where the calix[n]arene employed has only one functional site per cyclic member unit, the number of cyclic member units, n, will also be the number of arms, N, which may extend from the resultant core, i.e. N=n. Where there are two functional sites per cyclic member unit, there will, in theory, be twice as many arms, i.e., N=2n, and so forth depending upon the number of functional sites per cyclic member unit. Further, it will be appreciated that the calix[n]arene cores may be completely saturated, and therefore, are seen as being capable of providing the characteristics desired of cores for various applications, including viscosity improvers, and as being more readily controlled.

Generally, the calix[n]arene and derivatives thereof will have the basic structure where $R_4$ or $R_5$ must include at least a functional ester group (COOR', R' being a methyl or ethyl group) if an —OH terminus is found on the polymer to be connected thereto, or a functional allyl group ($CH_2CH=CH_2$) if an —SiH terminus is found on the polymer to be connected thereto. If one of $R_4$ or $R_5$ have the appropriate functional group, then the other of $R_4$ or $R_5$ may include a hydrogen or an alkyl having 1 to about 8 carbon atoms, although it will not necessarily be limited thereto. That is, $R_4$ and $R_5$ may be the same or different and is preferably selected from the group consisting of H, an alkyl having 1 to about 8 carbon atoms, an allyl, an alkoxy carbonyl, an alkoxy allyl, an alkoxy carbonyl methyl, a di(ethoxy carbonyl) ethyl, and a diallyl aminomethyl. It will also be appreciated that $R_4$ may not even be present when $R_5$ includes an appropriate functional group.

In the following subsections, various synthetic routes for the production of various useful calixarene derivatives suitable for use with preferred polyisobutylene and/or polysiloxanes are provided.

A. Calixarene Derivatives Suitable for Reaction with PIB-OH

Calixarene derivative cores suitable for use in conjunction with the present invention are those calix[n]arenes (n=4 to 16) having at least one functional ester group extending from each member unit of the calixarene core. Production of these calixarene derivatives are generally known in the art. In a preferred embodiment, one representative calix[8]arene derivative, 5,11,17, 23,29,35,41,47,-octa-tert-butyl-49,50, 51,52,53,54,55,56-octa(ethoxy carbonyl)-methoxy calix[8] arene, suitable for reaction with PIB-OH has the basic structure and may be prepared by placing about 111.2 g (0.72 mol) tert-butyl-phenol, about 27 g (1.2 mol) p-formaldehyde, about 1.6 mL (0.016 mol) 10N KOH, and about 600 mL xylene in a stirred, 1 L, 3-neck reactor which was heated to reflux the xylene for 4 hours, under a $N_2$ atmosphere. The reactor was equipped with a "Desk and Stark" water collector and condenser. After cooling to room temperature, the mixture was filtered, and solid product was washed consecutively with toluene, ether, acetone, and water. After drying, the mixture was recrystallized from chloroform. About 65.8 g of the product—colorless, glistening needles of p-tert-butylcalix[8]arene—was recovered. Purity was analyzed by GPC, and the results showed a monodisperse single peak.

Next, about 5 g p-tert-butylcalix[8]arene, about 5 g NaH, about 50 g β-bromo-ethoxyacetic acid, about 230 mL THF, and about 26 mL DMF was placed into a 500 mL, 3-neck reactor under a $N_2$ atmosphere. The reactor, equipped with a condenser, was stirred and heated. The reaction mixture was refluxed for 13 hours, then was cooled to room temperature. The suspension which formed was filtered. The excess of THF, DMF and β-bromo-ethoxyacetic acid of the filtrate was evaporated with a Rotavap, in vacuum. 100 mL water was then added to the residue, and it was extracted with $CHCl_3$ three times. The $CHCl_3$ phase was dried over $MgSO_4$ overnight and methanol was added (50 mL) to precipitate the product. The material was filtered, washed with methanol and dried. The yield, 5.87 g, was 76.7% 5,11,17,23,29,35,41,47,-octa-tert-butyl-49,50,51,52,53,54, 55,56-octa(ethoxycarbonyl)methoxy calix[8]arene.

Figure 1:
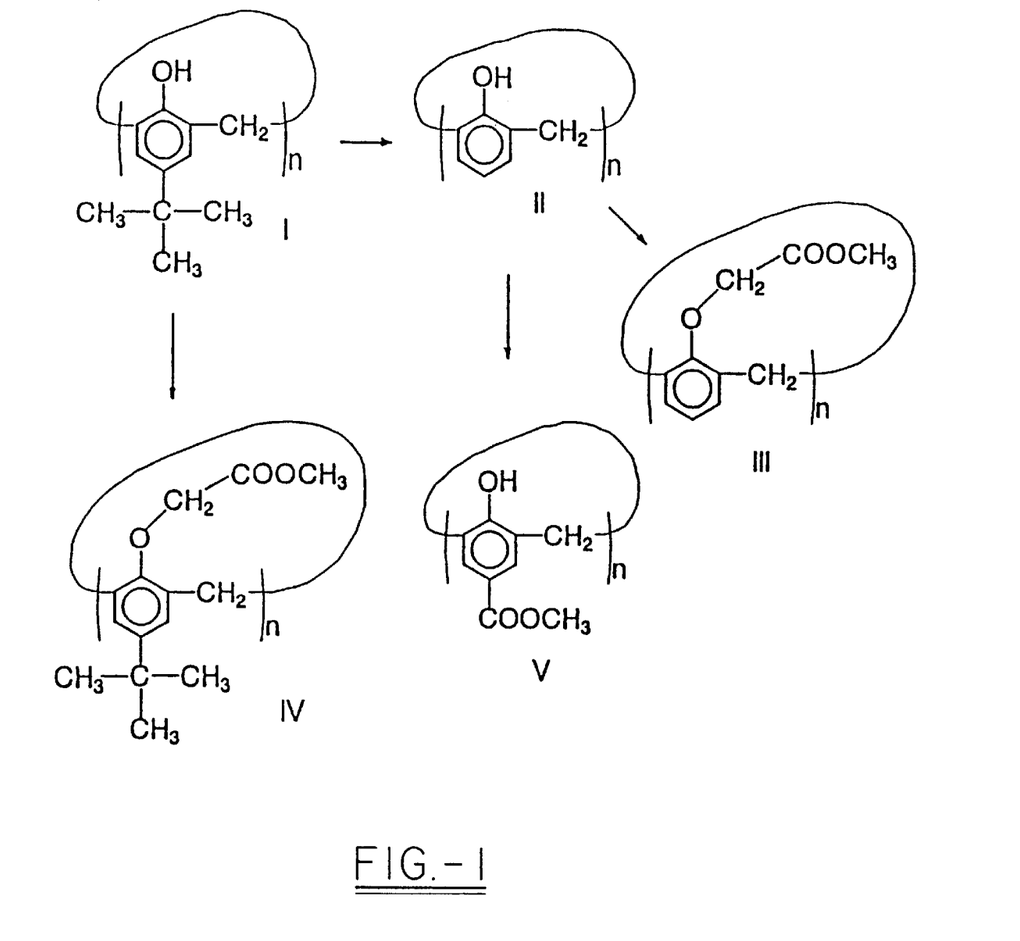
FIG. 1 is a schematic representation depicting various chemical routes for obtaining ester-derivatized calix[n]arenes.

This and other routes to the synthesis of calixarene cores suitable for use with PIB-OH arms can be seen in FIG. 1, the figure showing tert-butyl and hydrogen to be the alternative groups used in addition to the functional ester group. It will be appreciated that composition IV as shown in the FIG. 1 is the composition disclosed hereinabove. Compositions III, IV, and V, where n=8, are particularly preferred compositions.

Further detailed descriptions of the synthesis of these derivatives has been set forth in Gutsche, C. D., *Calixarenes*, The Royal Society of Chemistry, Thomas Graham House, Cambridge, (1989) and in Vicens, F. and B. Vohmer, eds., *Calixarenes: A Versatile Class of Macrocyclic Compounds*, Series of "Topics in Science", Kluwer Academic Publishers, Dordrecht (1991), the disclosures of which are incorporated herein by reference.

B. Calixarene Derivatives Suitable for Reaction with PDMS-SiH

For the formation of polysiloxane stars and particularly PDMS stars, the allyl derivatives of calix[n]arene where n=4 to 16 have been found to be suitable for reaction with PDMS-SiH. That is, calix[n]arenes where n= about 4 to 16 and having at least one functional allylic group extending from each member unit of the calixarene core are believed suitable for the present invention. Production of most of these calixarene derivatives are also, for the most part, known in the art, although certain derivatives noted hereinbelow are believed novel. In a preferred embodiment, one representative calix[8]arene derivative, 5,11,17,23,29, 35,41,47,-octa-tert-butyl-49,50,51,52,53,54,55,56-octaallyl oxycalix[8]arene, suitable for reaction with PDMS-SiH has the basic structure and may be prepared by placing about 111.2 g (0.72 mol) tert-butyl-phenol, about 27 g (1.2 mol) p-formaldehyde, about 1.6 mL (0.016 mol) 10N KOH, and about 600 mL xylene in a stirred, 1 L, 3-neck reactor which was heated to reflux the xylene for 4 hours, under a $N_2$ atmosphere. The reactor was equipped with a "Desk and Stark" water collector and condenser. After cooling to room temperature, the mixture was filtered, and solid product was washed consecutively with toluene, ether, acetone, and water. After drying, the mixture was recrystallized from chloroform. About 65.8 g of the product—colorless, glistening needles of p-tert-butylcalix[8]arene—was recovered. Purity was analyzed by GPC, and the results showed a monodisperse single peak.

Next, about 2.1 g (1.02 mmol) p-tert-butyl-calix[8]arene, about 2.05 g (85.4 mmol) NaH, about 30.0 g (248 mmol) allylbromide, about 100 mL THF, and about 10 mL DMF was placed into a 500 mL 3 neck reactor which was equipped with a condenser, and which was stirred and heated under a $N_2$ atmosphere. After reaching the reflux temperature, the reaction was stirred for 15 hours. After completing the reaction, about 200 mL ice water as added to the reaction mixture. The phases were then separated. The organic layer was worked up by evaporating the solvent and the solid residue was washed with toluene and then with methanol. The product was dried for 2 days in a vacuum oven. 2.11 g (65.8%) of the product, 5,11,17,23,29,35,41, 47,-octa-tert-butyl-49, 50,51,52,53,54,55,56-octaallyl oxycalix[8]arene, was obtained.

Figure 2:
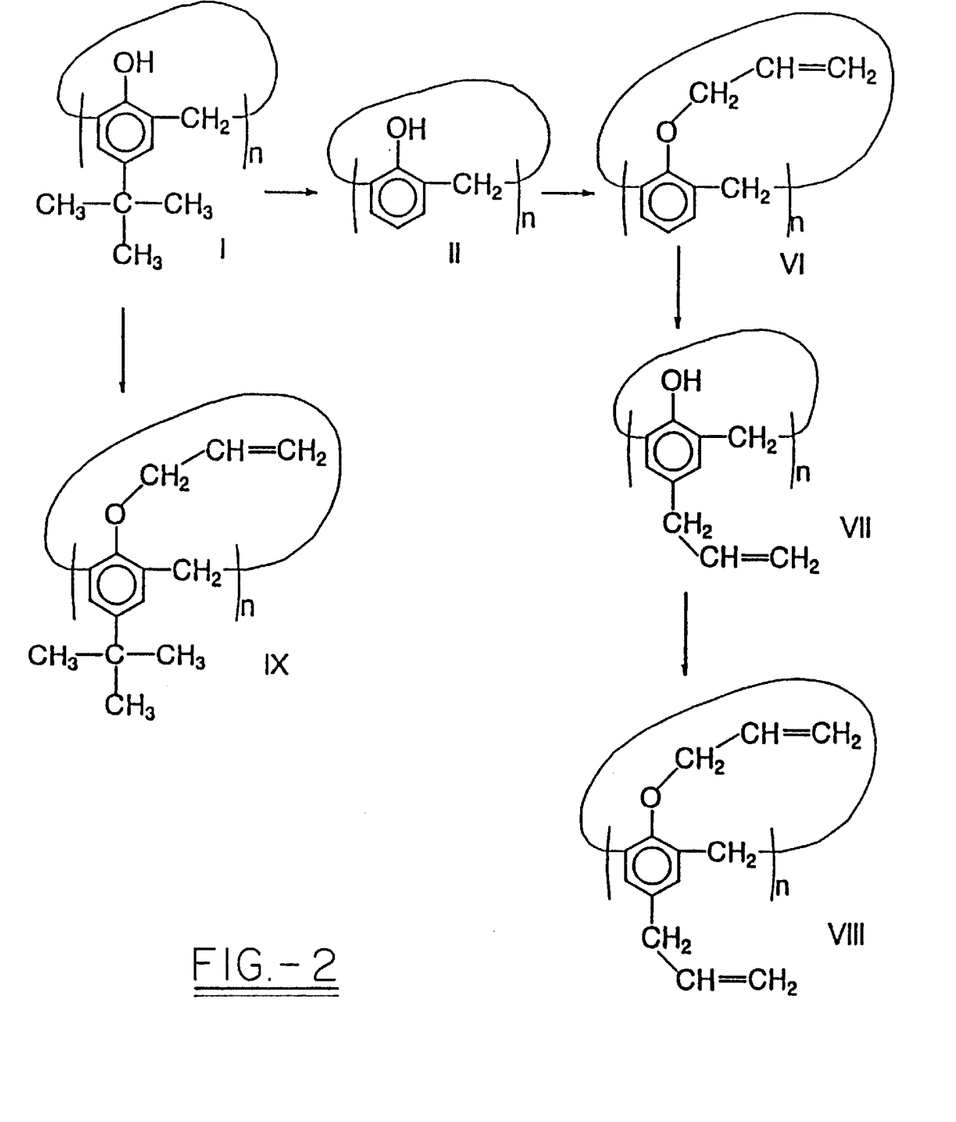
FIG. 2 is a schematic representation depicting various chemical routes for obtaining allyl-derivatized calix[n]arenes.

This and other routes to the synthesis of calixarene cores suitable for use with polysiloxane, and particularly PDMS-SiH, arms can be seen in FIG. 2, the figure showing tert-butyl and hydrogen to be the alternative groups used in addition to the functional allyl group. It will be appreciated that composition IX as shown in the FIG. 2 is the composition disclosed hereinabove. Compositions VI, VII, VIII, and IX, where n=8, are particularly preferred compositions.

It will be further appreciated that composition VIII has not yet been described in the literature and is believed new to the art. This composition also provides an example of a calix[n]arene core wherein each member unit has more than one functional group, i.e., two allyl groups, suitable for connecting to two separate, appropriate SiH-terminated polymer arms.

C. Derivatives Suitable for Reaction with both PIB-OH and PDMS-SiH

In yet another embodiment and as noted hereinabove, it will be appreciated that it is possible to attach a plurality of PIB and PDMS arms to a common calixarene-derivative core. However, in order to do so, the calixarene must be able to selectively and specifically react with both PIB-OH and PDMS-SiH. Thus, the calixarene core must carry both —OCH$_2$COOR', where R' is a methyl or ethyl group, and —CH$_2$CH=CH$_2$ substituents, or —OCH$_2$CH=CH$_2$ and CH$_2$COOR', where R' is a methyl or ethyl group, substituents.

Figure 3:
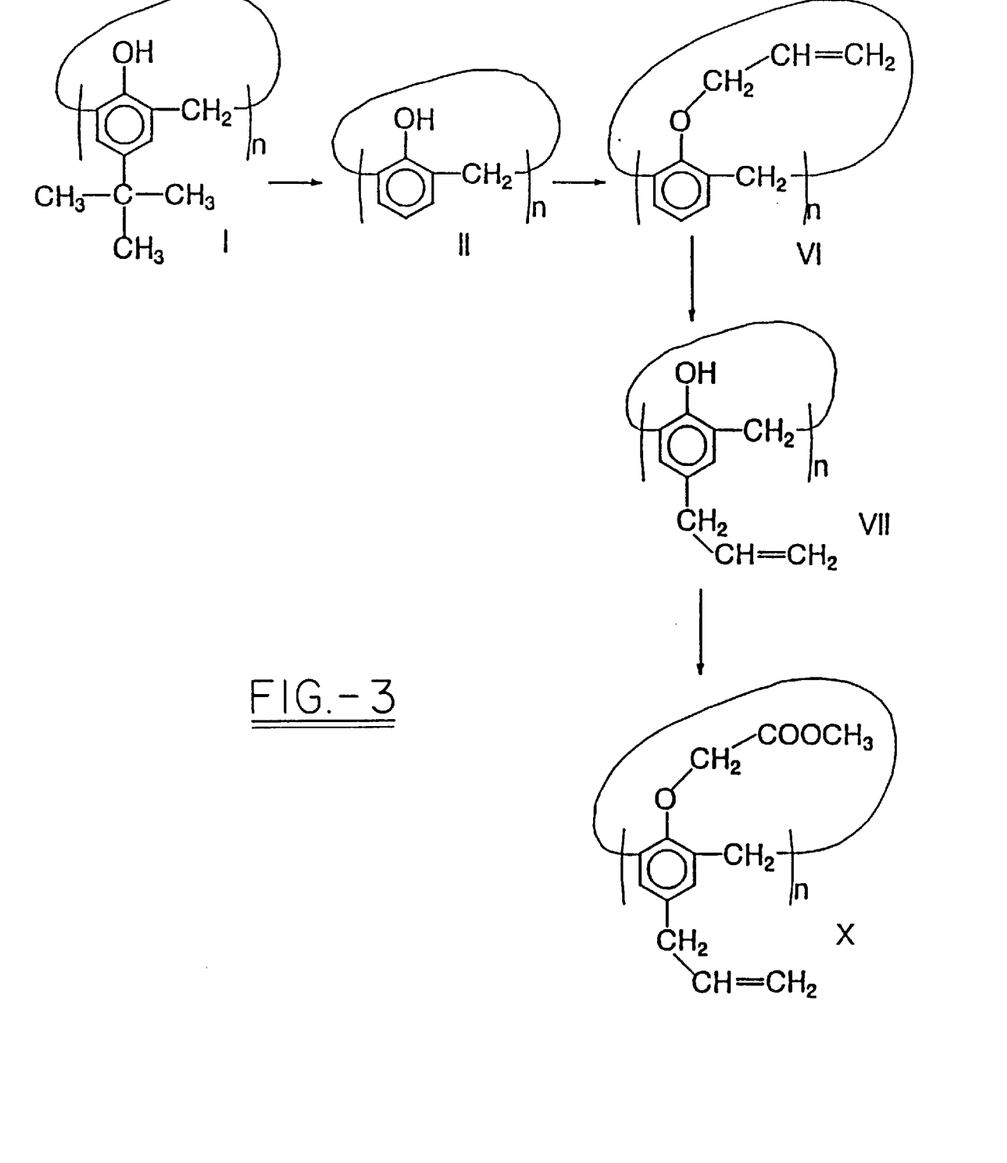
FIG. 3 is a schematic representation depicting a chemical route to obtaining a calix[n]arene derivative having an ester group and an allylic group.

FIG. 3 shows one route by which such a calixarene core can be prepared. With reference to this FIG. 3, it will be appreciated that the synthesis of the starting material shown is known in the art and was disclosed hereinabove in the production of the other calixarene cores. Thereafter, dealkylation (second structure) of the starting material can be carried out by other well known methods such as are described in Gutsche, C. D. and L. G. Lin, "Calixarenes 12 The Synthesis of Functionalized Calixarenes" *Tetrahedron* 42(6), 1633 (1986), for example. The allyl group may then be introduced (third structure) by still other known methods. See, for instance, Bohmer V. and P. O'Sullivan, *Trends in Polymer Science*, 1(9) 267 (1993); and Dhawan, B. et al., *Macromol. Chem.*, 188, 921 (1987). Isomerization by Claisen rearrangement (fourth structure) may then be effected by Gutsche et al.'s procedures as disclosed in Gutsche, C. D. and F. A. Levine, *J. Am. Chem. Soc.*, 104, 2652 (1982); Gutsche C. D., et al. *J. Org. Chem.*, 50, 5802 (1985); and Gutsche, C. D., *Aldrichimica Act.*, 28(1), 1 (1995), the disclosures of which are incorporated herein by reference. Finally, the ester group is introduced (fifth structure) by Ungaro et al.'s routes as described in Arduini, A. et al., *Chem. Soc. Chem. Commun.*, 981 (1984); Ungaro, R., et al., *J. Incl. Phenom.*, 2, 199 (1984); and Arduini, A. et al., *Tetrahedron*, 42, 2089, (1986). The calixarene ring core containing both the ester and allyl substituents can be now used as the starting material for the sought multi-arm star carrying both PIB and PDMS arms.

(III) LINKING MULTIPLE ARMS TO A CORE

To link the polymer arms prepared hereinabove to the core prepared separately hereinabove, one of two processes may be used depending upon the type of polymer arm employed. That is, two general, well-known, chemical reactions have been identified which can be used to link quantitatively multiple PIB-OH or PDMS-SiH arms to calixarene cores. A discussion of these chemistries follows.

A. Linking PIB-OH with Calixarenes Containing Ester Groups

It has been found that hydroxyl-terminated polyisobutylene arms, and particularly PIB-OH arms, can be quantitatively linked to ester-derivatized calixarenes by transesterification in the presence of a catalyst. Transesterification reactions are well known in the art and can be carried out essentially quantitatively. Detailed descriptions of this process are more particularly set forth in various journals and patents, including Nishimura, A. A., and H. Komagata, *F. Macromol. Sci. (Chem.)*, A1(4), 617 (1967) and U.S. Pat. Nos. 2,720,502, 2,843,567, and 4,845,158, the disclosures of which are incorporated herein by reference.

In the preferred embodiment wherein PIB-OH is linked to a calix[8]arene derivative having an ester group in the presence of the catalyst tetra(n-butoxy) titanate, the transesterification reaction may be shown as follows.

where R$_4$ may be any of those groups disclosed for R$_4$ hereinabove, but is preferably a tert-butyl group.

Any conventional catalyst known in the art suitable for catalyzing the transesterification process may be used in the present, but most preferred is the common catalyst tetra(n-butoxy)titanate.

B. Linking PDMS-SiH with Calixarenes Containing Allyl Groups

It has been found that SiH-terminated polysiloxane arms, and particularly PDMS-SiH arms, can be quantitatively linked to allyl-derivatized calixarenes by hydrosilation in the presence of a catalyst. Such hydrosilation reactions are well known in the art and can be carried out essentially quantitatively. Detailed descriptions of this process are more particularly set forth in various journals and patents, including Fang, T. R., and J. P. Kennedy, *Polym. Bull.*, 10, 82 (1983) and U.S. Pat. Nos. 4,642,362 and 4,699,966.

In the preferred embodiment wherein PDMS-SiH is linked to a calix[8]arene derivative having an allyl group in the presence of the catalyst hexachloroplatinic acid monohydrate (H$_2$PtCl$_6$), the hydrosilation reaction may be shown as follows.

where $R_4$ may be any of those groups disclosed for $R_4$ hereinabove, but is preferably a tert-butyl group.

Any conventional catalyst known in the art suitable for catalyzing the hydrosilation process may be used in the present, but most preferred are the common catalyst Karstedt's catalyst or hexachloroplatinic acid monohydrate.

C. Linking PIB-OH and PDMS-SiH with Calixarenes Containing Both Ester and Allyl Groups It will also be appreciated that, where the calixarene compound includes both a functional ester group and an allylic group, both transesterification and hydrosilation processes may be used to link a plurality of PIB-OH arms to the ester group, and a plurality of PDMS-SiH arms to the allylic group, respectively. Preferably, the synthesis occurs in two steps: 1) transesterification of the methyl ester with PIB-OH, followed by 2) hydrosilation of the allyl substituent with PDMS-SiH. The transesterification and hydrosilation can be carried out by the same procedures as discussed hereinabove.

In order to demonstrate practice of the invention, a novel multi-arm star polymer comprising a plurality of SiH-terminated polysiloxane arms linked by hydrosilation to a calix[8]arene (an 8-membered cyclic ring structure) derivative core containing allyl groups were prepared according to the concepts of the present invention. The following is a detailed description of the process used for carrying out the present invention. It will be appreciated that this description is illustrative only and not meant to limit the invention, as measured by the scope and spirit of the claims.

Figure 4:
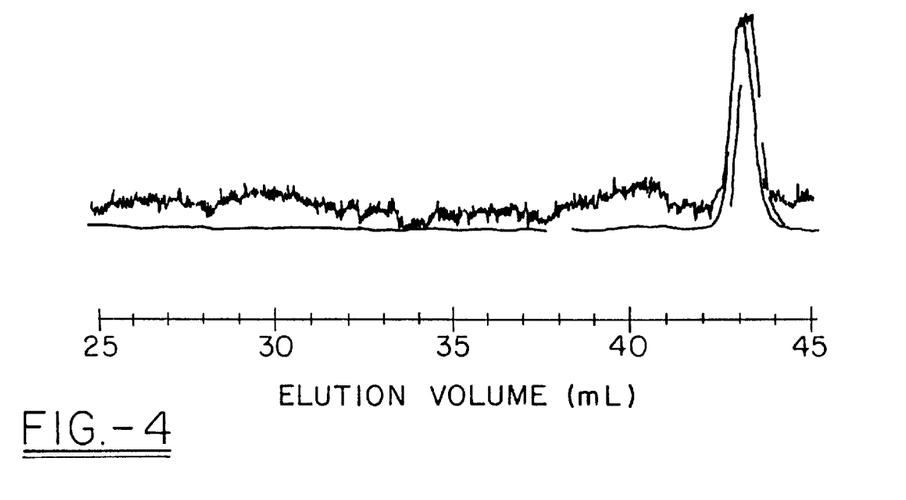
FIG. 4 is a set of gel permeation chromatograms of (a) a trace of the refractive index (RI) signal, (b) a trace of the UV signal, and (c) a trace of the laser light scattering (LLS) signal showing the presence of an allyl-derivatized calix[8] arene core before reaction with any polymer at about 43 mL of Elution Volume.

Initially, an allyl-derivatized calix[8]arene having the structure was analyzed by GPC equipped with refractive index (RI), ultraviolet (UV) and laser light scattering (LLS) detectors. As depicted in FIG. 4, a series of gel permeation chromatograms of (a) a trace of the refractive index (RI) signal, (b) a trace of the ultraviolet (UV) signal, and (c) a trace of the laser light scattering (LLS) signal of the calix[8]arene showed the presence of the calixarene core at about 43 mL of Elution Volume.

Figure 5:
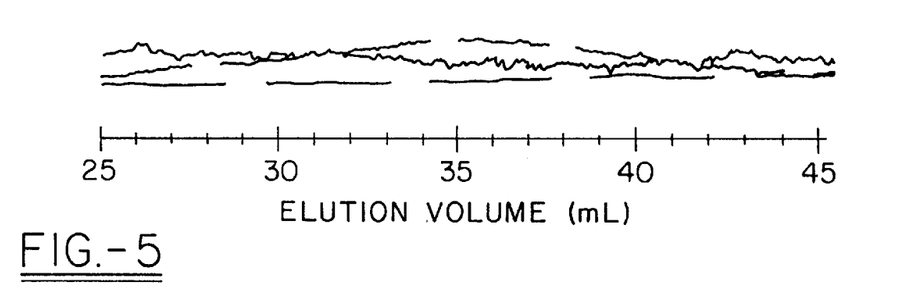
FIG. 5 is a set of gel permeation chromatograms of (a) a trace of the refractive index (RI) signal, (b) a trace of the UV signal, and (c) a trace of the laser light scattering (LLS) signal of the PDMS-SiH pre-arm in THF solvent at room temperature.

In a similar manner, GPC analysis was also conducted on the PDMS-SiH prearm in THF solvent at room temperature. The PDMS-SiH prearm had a number average degree of polymerization, $DP_n$, of about 60. As shown in FIG. 5, the gel permeation chromatograms of the traces of (a) the RI signal, (b) the UV signal, and (c) the laser light scattering (LLS) signal of the PDMS-SiH pre-arm in THF solvent showed no signal under the conditions employed.

Next, about 0.104 g ($6.44 \times 10^{-5}$ mol) of the allyl-derivatized calix[8]arene; about 22.7 g ($5.03 \times 10^{-3}$ mol) PDMS-SiH; about 6 $\mu$L $H_2PtCl_6 \cdot H_2O$ catalyst solution, which is equivalent to about 100 ppm Pt per allylic double bond; and about 10 mL ($9.4 \times 10^{-2}$ mol) toluene was placed into a 100 mL 3 neck round-bottom flask fitted with a magnetic stirring bar, nitrogen inlet/outlet tube, and reflux condenser. The toluene solvent was dried over $CaCl_2$ and freshly distilled from $CaH_2$ under $N_2$. The flask was then placed in a heated temperature controlled oil bath. The light yellow somewhat viscous solution was heated to 90° C. and stirred, and a series of samples (~30 mg) were withdrawn by a dried Pasteur pipet at initiation of the reaction and after about 0.5, 3, 17.25, 44, 68, 92, 116, 140 and 164 hours of reaction. Each sample was then added or otherwise dissolved in 4 mL THF. The resulting solutions were then analyzed by GPC.

Figure 6:
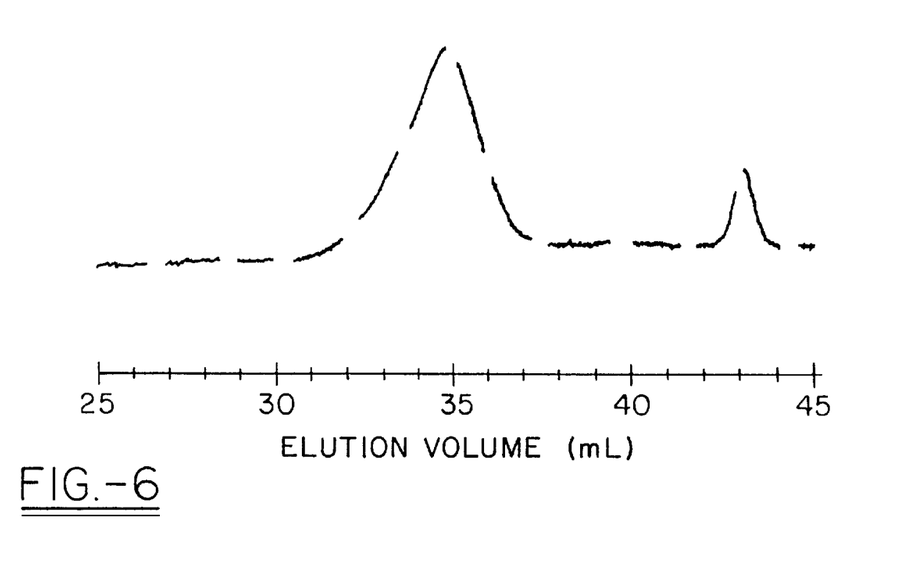
FIG. 6 is a gel permeation chromatogram of a UV trace of a sample of the resultant octa-PDMS-arm, calix[8]arene-core, star polymer approximately 0.5 hours after initiation of a hydrosilation reaction.
Figure 7:
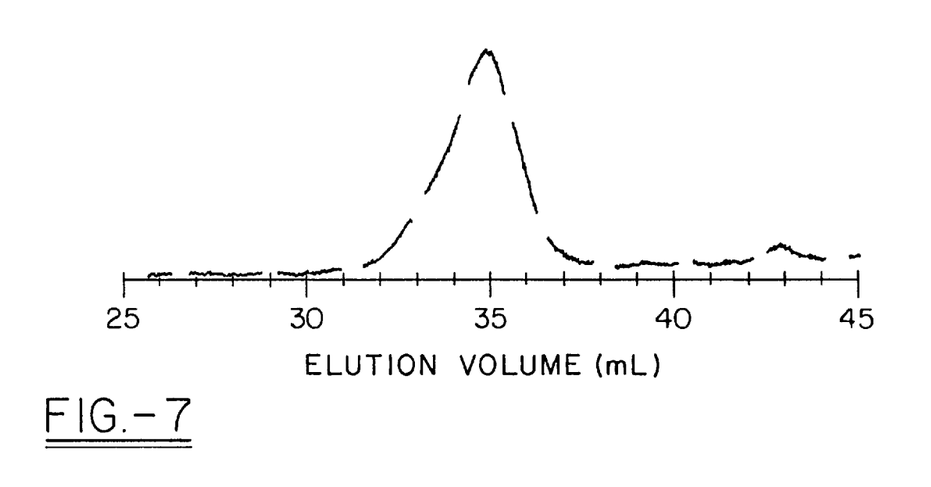
FIG. 7 is a gel permeation chromatogram of a UV trace of another sample of the resultant octa-PDMS-arm, calix[8]arene-core, star polymer approximately 3 hours after initiation of the hydrosilation reaction.

As can be seen in FIGS. 6 and 7, the UV trace of the resultant octa-PDMS-arm, calix[8]arene-core, star polymer sample withdrawn approximately 0.5 hours after initiation of the hydrosilation reaction (FIG. 6.) showed the presence of some unreacted calixarene (small peak at ~43 mL Elution Volume) but, more importantly, also showed the presence of the desired star (a relatively large peak at ~35 mL Elution Volume). After 3 hours of reaction (FIG. 7), the UV trace showed only a very small amount (1–2%) of unreacted calixarene (at ~43 mL Elution Volume) while at the low elution volume of ~35 mL, an even larger signal was present, indicating the presence of a significantly large amount of the high molecular weight, octa-PDMS-arm, calix[8]arene-core, star product. Evidently, arm linking by hydrosilation is practically complete after about 3 hours of reaction, and indeed, the UV scans collected after this time did not change.

Notably, the scans of the samples obtained showed only UV signals but no RI or LLS signals because of the low core concentrations (>1 mg/mL) used in the GPC runs. Assuming that hydrosilation was essentially quantitative, this UV spectroscopy evidence is clear proof of the formation or the desired multi-arm product: Octa-PDMS-arm, calix[8]arene-core star.

Thus it should be evident that the methods of the present invention are highly effective in synthesizing star polymers having well-defined calixarene cores via the "arm and core first" method. The invention is particularly suited for the production of polyisobutylene and polysiloxane stars, but is not necessarily limited thereto. Even more particularly, it has been demonstrated that OH-terminated PIB arms and SiH-terminated PDMS arms may be linked to ester derivatives of calixarenes and allyl derivatives of calixarenes, respectively, via the processes of transesterification and hydrosilation, respectively. Such multi-arm star polymers are seen as having utility as motor oil additives and the like, although it will be appreciated that the subject star polymers may be readily useful in a variety of applications, including the manufacture of other materials as well. Still further, it will be appreciated that linking OH-terminated PIB prearms and SiH-terminated PDMS prearms to ester derivatives of calixarenes and allyl derivatives of calixarenes, respectively, provides well-defined star polymers having well-defined cores. Furthermore, because the arms and cores are readily controlled, the molecular weight of the polymer arms, and therefore, the molecular weight of the stars can be readily controlled. The resultant star polymers are believed to have a more definite molecular weight, a more definite number of arms, and a narrower polydispersity than other star polymers previously developed.

Based upon the foregoing disclosure, it should now be apparent that the novel star polymers described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, calixarenes employed according to the present invention are not necessarily limited to calix[8]arenes and may be prepared based by any method known in the art. Moreover, the polyisobutylene and polysiloxane arms of the present invention may be prepared based upon a variety of methods. Thus, the scope of the invention shall include all modifications and variations that may fall within the scope of the attached claims.

What is claimed is:

1. A star polymer comprising:
    a core component selected from the group consisting of calix [n] arenes where n=4 to 16 and derivatives thereof; and
    at least three polymer arms connected to said core component.

2. A star polymer, as set forth in claim 1, wherein at least one of said polymer arms is selected from the group consisting of polyisobutylene and polysiloxane.

3. A star polymer, as set forth in claim 1, wherein said core component is selected from the group consisting of calix[n] arenes where n=4, 6 or 8 and derivatives thereof.

4. A star polymer, as set forth in claim 1, wherein said core component is selected from the group consisting of calix[n] arenes where n=6 to 16 and derivatives thereof.

5. A star polymer, as set forth in claim 1, wherein said core component is selected from the group consisting of calix[8] arene and derivatives thereof.

6. A star polymer, as set forth in claim 2, wherein a plurality of said polymer arms is polyisobutylene.

7. A star polymer, as set forth in claim 2, wherein said at least three polymer arms are polysiloxane.

8. A star polymer, as set forth in claim 2, wherein a plurality of said polymer arms is polyisobutylene and a second plurality of said polymer arms is polysiloxane.

9. A star polymer, as set forth in claim 2, wherein said at least three polymer arms are polydimethylsiloxane (PDMS).

10. A method for the synthesis of polyisobutylene star polymers comprising
    linking a plurality of hydroxyl-terminated polyisobutylene arms to a core component selected from the group consisting of calixarenes and derivatives thereof, wherein the core component has from about 4 to 16 member units and includes at least one functional ester group extending from each member unit, each polyisobutylene arm being linked to one of the ester groups of the core component by transesterification in the presence of a catalyst.

11. A method, as set forth in claim 10, wherein said polyisobutylene arms are monohydroxyl terminated polyisobutylene arms.

12. A method, as set forth in claim 10, wherein said core component has from about 6 to 16 member units.

13. A method, as set forth in claim 10, wherein said core component has 8 member units.

14. A method, as set forth in claim 13, wherein one polyisobutylene arm is linked to each member unit of said core component to form an octa-polyisobutylene arm, calix [8]arene core star polymer.

15. A method, as set forth in claim 10, wherein said catalyst is tetra(n-butoxy) titanate.

16. A method for the synthesis of polysiloxane star polymers comprising
    linking at least three SiH-terminated polysiloxane arms to a core component selected from the group consisting of calix arenes and derivatives thereof, wherein the core component has from about 4 to 16 member units and includes at least one functional allyl group extending from each member unit, each polysiloxane arm being linked to one of the allyl groups of the core component by hydrosilation in the presence of a catalyst.

17. A method, as set forth in claim 16, wherein said polysiloxane arms are polydimethylsiloxane arms.

18. A method, as set forth in claim 16, wherein said core component has from about 6 to 16 member units.

19. A method, as set forth in claim 16, wherein said core component has 8 member units.

20. A method, as set forth in claim 19, wherein one polysiloxane arm is linked to each member unit of said core component to form an octa-polysiloxane arm, calix[8]arene core star polymer.

21. A method, as set forth in claim 16, wherein said catalyst is selected from the group consisting of Karstedt's catalyst and hexachloroplatinic acid monohydrate.

22. A method for the synthesis of star polymers containing polyisobutylene and polysiloxane arms emanating from a core, comprising
    linking a plurality of hydroxyl-terminated polyisobutylene arms and a plurality of SiH-terminated polysiloxane arms to a core component selected from the group consisting of calixarenes and derivatives thereof, wherein the core component has from about 4 to 16 member units and includes at least one functional ester group extending from each member unit and at least one functional allyl group extending from each member unit, each polyisobutylene arm being linked to one of the ester groups of the core component by transesterification in the presence of a first catalyst, and each polysiloxane arm being linked to one of the allyl groups of the core component by hydrosilation in the presence of a second catalyst.

23. A method, as set forth in claim 22, wherein said polysiloxane arms are polydimethylsiloxane arms.

24. A method, as set forth in claim 22, wherein said core component has from about 6 to 16 member units.

25. A method, as set forth in claim 22, wherein said core component has 8 member units.

26. A method, as set forth in claim 22, wherein said first catalyst is tetra(n-butoxy) titanate.

27. A method, as set forth in claim 22, wherein said second catalyst is selected from the group consisting of Karstedt's catalyst and hexachloroplatinic acid monohydrate.

\* \* \* \* \*